(12) United States Patent
Chaykovskyy et al.

(10) Patent No.: US 10,512,412 B2
(45) Date of Patent: Dec. 24, 2019

(54) METHOD OF ECG EVALUATION BASED ON UNIVERSAL SCORING SYSTEM

(71) Applicants: Illya Anatoliiovych Chaykovskyy, Kiev (UA); Mykola Mykolaiovych Budnyk, Kyiv (UA); Ganna Anatoliivna Starynska, Kyiv (UA)

(72) Inventors: Illya Anatoliiovych Chaykovskyy, Kiev (UA); Mykola Mykolaiovych Budnyk, Kyiv (UA); Ganna Anatoliivna Starynska, Kyiv (UA)

(73) Assignee: CARDIOLYSE OY, Helsinki (FI)

( * ) Notice: Subject to any disclaimer, the term of this patent is extended or adjusted under 35 U.S.C. 154(b) by 122 days.

(21) Appl. No.: 15/743,282

(22) PCT Filed: Sep. 30, 2015

(86) PCT No.: PCT/UA2015/000080
§ 371 (c)(1),
(2) Date: Jan. 10, 2018

(87) PCT Pub. No.: WO2017/010963
PCT Pub. Date: Jan. 19, 2017

(65) Prior Publication Data
US 2018/0199845 A1    Jul. 19, 2018

(30) Foreign Application Priority Data

Jul. 13, 2015 (GB) .................................. 2015 06895

(51) Int. Cl.
*A61B 5/04* (2006.01)
*A61B 5/0452* (2006.01)
*A61B 5/024* (2006.01)
*A61B 5/16* (2006.01)
*A61B 5/00* (2006.01)
(Continued)

(52) U.S. Cl.
CPC .......... *A61B 5/0452* (2013.01); *A61B 5/0245* (2013.01); *A61B 5/02405* (2013.01); *A61B 5/04012* (2013.01); *A61B 5/165* (2013.01); *A61B 5/7275* (2013.01); *G16H 50/30* (2018.01)

(58) Field of Classification Search
CPC ... A61B 5/0452; A61B 5/0245; A61B 5/7275; A61B 5/04012; A61B 5/02405; A61B 5/165; G16H 50/20; G16H 50/30
See application file for complete search history.

(56) References Cited

PUBLICATIONS

Ç haikovsky I. A. Analiz elektrokardiogrammy v odnom, shesti i dvenadtsati otvedeniya s tochki zreniya informatsionnoi tsennosti: elektrokardiograficheskiy kaskad. Klinicheskaya informatika i Telemeditsina, 2013, T.9, Vyp. 10, p. 49-55.

*Primary Examiner* — Mallika D Fairchild
(74) *Attorney, Agent, or Firm* — John Alumit

(57) ABSTRACT

The invention is designed to diagnose cardiovascular system (CVS) based on at least 148 quantitative ECG parameters including Heart Rate Variability (HRV) ones. Parameters are rated to 100 points, divided into 7 groups with close physiological nature, 4 diagnostic criteria (evaluation of CVS regulation, myocardium state, emotion state, HR disorders) and complex index of functional state (CIFS) are calculated. Aggregated diagnostic and prognostic decision are made about the functional CVS state and psycho-emotional state by combining CIFS, Hannover (or other similar algorithm), Minnesota code, myocardial abnormalities codes, and prediction codes of serious cardiovascular events. The method increases the accuracy and reliability of diagnostics.

3 Claims, 4 Drawing Sheets

(51) Int. Cl.
*G16H 50/30* (2018.01)
*A61B 5/0245* (2006.01)

| Quantitative parameter | Patient B | | Patient 0301 | | Patient 0304 | |
|---|---|---|---|---|---|---|
| | % | Decision | % | Decision | % | Decision |
| Heart rate, beats/minute | 70 | normal range | 78 | normal range | 68 | normal range |
| SDNN, ms | 79 | normal range | 39 | normal range | 22 | moderate decreased |
| RMSSD, ms | 33 | normal range | 26 | mild decrease | 15 | |
| Stress index | 71 | normal range | 162 | mild increase | 274 | moderate increase |
| Triangular index | 10,08 | normal range | 10.34 | normal range | 24.8 | normal range |
| Emotional state index | 0,35 | neutral | 0.52 | neutral | 0.47 | neutral |
| PNN50, % | 8 | mild decrease | 8 | mild decrease | 1 | severe decrease |
| Autonomic balance | 1,1 | normal range | 1.21 | normal range | 2.66 | normal range |
| Activity of vasomotor regulation cycle | 47 | mild increase | 28 | normal range | 30 | normal range |
| Activity of sub-cortical regulation levels | 3 | normal range | 2 | mild decrease | 3 | normal range |
| Entropy | 0,42 | normal range | 0.56 | normal range | 0.41 | normal range |
| Fractal index | 0,53 | mild decrease | 0.94 | normal range | 0.68 | mild decrease |
| Functional classes: | | | | | | |
| by Baevsky | 2 | normal range | 4 | functional stress | 1 | normal range |
| by Mashyn | 1 | normal range | 2 | general stress | 1 | normal range |
| Integral indicators of ST-T form for: | | | | | | |
| Lead I | 77 | normal range | 62 | minor damage | 44 | moderate damage |
| Lead III | 62 | minor damage | 80 | normal range | 63 | minor damage |
| Lead AvL | 64 | minor damage | 65 | Minor damage | 45 | moderate damage |
| Lead AvR | 95 | normal range | 70 | minor damage | 58 | minor damage |
| ECG phase ratio index | 76 | normal range | 49 | moderate damage | 0 | severe damage |
| Indexes of peaks and areas of QRS ECG for: | | | | | | |
| Lead I | 87 | normal range | 56 | minor damage | 54 | minor damage |
| Lead II | 87 | normal range | 76 | normal range | 53 | |
| Lead III | 50 | moderate damage | 47 | moderate damage | 30 | moderate damage |
| Lead AvL | 83 | normal range | 69 | minor damage | 44 | moderate damage |
| Lead AvR | 88 | normal range | 51 | minor damage | 61 | minor damage |
| Lead AvF | 78 | normal range | 60 | minor damage | 43 | moderate damage |
| ECG interval size index | 94 | normal range | 86 | normal range | 88 | normal range |
| QRS-T angle in the frontal plane | 0 | normal range | 25 | minor damage | 57 | severe damage |

Figure 2

|  | Patient B | | Patient 0301 | | Patient 0304 | |
|---|---|---|---|---|---|---|
|  | Point | Decision | Point | Decision | Point | Decision |
| General indicator | Level 2 | | | | | |
| 1- Current control of myocardial status | 95 | normal range | 50 | moderate damage | 49 | moderate damage |
| 2 - Current control of CS regulation | 96 | normal range | 80 | normal range | 42 | moderate damage |
| 3 - Current control of cardiovascular status | 81 | normal range | 79 | normal range | 59 | minor damage |
| 4 – Myocardial reserve evaluation | 65 | minor damage | 91 | normal range | 71 | minor damage |
| 5 – Reserve of CVS regulation | 94 | normal range | 97 | normal range | 52 | minor damage |
| 6 - Psycho-emotional state | 80 | normal range | 76 | normal range | 39 | moderate damage |
| 7 – State of CVS reserve | 89 | normal range | 83 | normal range | 55 | minor damage |
| Diagnostic criterion | Level 3 | | | | | |
| 1 – Myocardial state | 80 | normal range | 70 | minor damage | 45 | moderate damage |
| 2 – CVS regulation evaluation | 95 | normal range | 89 | normal range | 47 | moderate damage |
| 3 – Cardiac arrhythmias | 85 | none (normal range) | 81 | none (normal range) | 57 | minor damage |
| 4 - Emotional state evaluation | 80 | normal range | 76 | normal range | 39 | moderate damage |

Figure 3

| Diagnostic criterion | Patient B | | Patient 0301 | | Patient 0304 | |
|---|---|---|---|---|---|---|
| | Point | Decision | Point | Decision | Point | Decision |
| Level 4 | | | | | | |
| Complex index of functional state (CIFS) | 85 | normal range | 79 | normal range | 47 | moderate damage |
| Hannover algorithm | 100 | normal range | 75 | minor damage | 50 | moderate damage |
| Minesotta code | 100 | normal range | 50 | moderate damage | 55 | minor damage |
| Myocardial abnormalities code | | | | | | |
| Silvester code | 94 | normal range | 80 | normal range | 52 | minor damage |
| Q-code | 87 | normal range | 73 | minor damage | 45 | moderate damage |
| CIIS code. | 80 | normal range | 69 | minor damage | 47 | moderate damage |
| Aldridge code | 95 | normal range | 71 | minor damage | 56 | minor damage |
| Prediction code of serious cardiovascular events | | | | | | |
| Froelicher code | 90 | normal range | 76 | normal range | 47 | moderate damage |
| 1st lead code of | 90 | normal range | 70 | minor damage | 49 | moderate damage |
| AVR lead code | 100 | normal range | 85 | normal range | 53 | minor damage |
| Prediction code of sudden cardiac death | 83 | normal range | 68 | minor damage | 41 | moderate damage |
| Level 5 | | | | | | |
| Aggregated decision | 91 | normal range | 72 | minor damage | 49 | moderate damage |

Figure 4

METHOD OF ECG EVALUATION BASED ON UNIVERSAL SCORING SYSTEM

FIELD OF INVENTION

This invention relates to medicine in particular to functional diagnostics and can be used for functional and diagnostic research for the human cardiovascular system (CVS) in order to detect signs of its pathology.

PRIOR STATE-OF-ART

Objective and comprehensive assessment of abnormalities and identification of a degree of damages of the CVS are of great current interest. This system is vital life support system and serves as human adaptive capacities indicator because it ensures the circulatory system of blood vessels—arteries, veins and capillaries penetrating all over the tissues and organs of the body. Heart's pumping action ensures the blood movement and the main part of the heart performing the major role in blood pumping throughout the vessels of human body is the myocardium (heart muscle).

The CVS functioning level is the essential indicator reflecting the state of the whole body and keeping the balance within the environment. Therefore, further improvements in reliability and comprehensive diagnosis of early signs of pathology of the human cardiovascular system by involving non-invasive instrumental methods when abnormalities is weak or hidden (asymptomatic) forms are the task of vital importance.

At the present time the ECG method is developed in rapid manner and remains one of the core and the most widely used methods to diagnosis the CVS and the myocardium. Thereby, the promising direction towards the CVS diagnosis is to improve the methods of ECG automatic analysis that conveys a large amount of information about the functional state of CVS.

Quantitative method for the CVS evaluation by ECG is well known [RU 2,210,406, A61B5/0452, Cardiovascular functional state assessment method by rhythmical interaction of ECG variations. A. S. Radchenko, 2003] and using active orthostatic test. This CVS functional state (FS) evaluation is carried out through continuous ECG registration within the 1st standard lead starting from the moment when a subject takes vertical body position in order to determine the end of the transition process in heart rhythm and furthermore during 3 minutes period or more to select the ECG recording interval having stationarity and ergodicity conditions. PQ, QT and TP intervals are measured and evaluated their stationarity and the degree of consistency on the basis of frequency, phase and coherent analysis (auto, mutual and phase spectra, coherence spectra), and the calculated data are compared with standard values. In such a way, based on analysis of interaction of variations of various ECG rhythms, to predict degree of efficiency of adaptive response to cyclic exercise load without imposing the load itself.

The advantage of this method is to use many of amplitude-time parameters, to assess their interaction (coherence) under load by means of calculating of different types of spectra.

Disadvantages of this method are:
1) it does not evaluate the state of cardiovascular regulation, the state of myocardium and integral index of the functional state of CVS,
2) it is applied only under physical activity;
3) normalization of parameters onto heart rate (HR) value is absent,
4) it is characterized by rather complicated calculations.

The wider diagnostic potential is implemented in RU 2,151,545 [A61V5/02, Functional state evaluation method of cardiovascular and vegetative nervous systems (VNS), L. M. Makarov, 2000], in which according to Holter ECG monitoring the average HR values are calculated separately during periods of sleep and activity, and these calculations serve the basis for determining the circadian index (CI) as the daily-to-night ratio of average HR value per minute. CI values 1.24-1.44 indicate about stability in daily (circadian) rhythm for healthy subjects and patients with no severe abnormalities of intracranial or vegetative regulation centers of one-day rhythm of cardiac activity. The CI value as serving to characterizes CVS and VNS states do not depend on neither age and sex of the subjects nor the main rhythm and the applied equipment respectively.

The advantage of this approach is to take into account the heart activity regulation to be made by VNS. The disadvantages of this method is reduce of its information value and limit in its use. They are:
1) myocardium parameters are not taken into account whose role to characterize its state and only HR is measured. The HR is the simplest parameter describing HR variability (HRV) measured by the number of time intervals between heart beats;
2) no way to evaluate the state of CVS regulation,
3) no calculation of the integral index of the CVS functional state.

Moreover, there is well-informative method to diagnose heart functional state according to UA 54185 [A61B 5/0452, A61B 5/02, Method to assess physiological value of psycho-emotional or physical load, I. A. Chaykovskyy, M. M. Budnyk, 2010]. In above method ECG data at one or more standard leads are recorded under 3 states (rest, load, restitution) to determine HR and 10 amplitude-time parameters of ECG curve (amplitude of Q, R, S, T waves, amplitude ratio R/S, length of Q peak, QRS complex, PQ and QT intervals, T wave symmetry), then these 10 parameters are normalized as to HR and calculated ratio for "load/rest" and "load/restitution" states. Next it is determined the degree of physiological value of increased (decreased) load: low degree when all ratio are less than 0.8 or more than 1.2, average (high) degree—if at least one ratio is in the range of 0.8-1.2 (more than 1.2 or less than 0.8). Thereby it is concluded that the physiological value of the load is low (average or high) when values of increase and decrease are low degree (at least one from value has average or high degree).

The advantage of the approach under UA 54,185, in contrast to RU 2,151,545, is normalization onto HR of 10 amplitude-time ECG parameters which characterize the myocardium state. Disadvantages are as follows:
1) HR is only used to normalization but not as diagnostic parameter,
2) do not use other than HR parameters of HRV,
3) it is only applied 2 diagnostic decisions—the norm (stability) or deviations from the norm, i.e. it uses the simplest threshold rule not permitting to assess a degree of cardiovascular functional state.

These drawbacks have been partially corrected at UA 61285 [A61B 5/0452, A61B 5/02, Method for evaluation of heart functional state based on ECG analysis and HRV, I. A. Chaykovskyy, M. M. Budnyk, 2011]. ECG is recorded and parameters are calculated similar to UA 54,185. It differs from those that within the purpose for making the evaluation the calculation of specified parameters, area approximation coefficients are made to obtained individual reference state of human heart via averaging these parameters being received during at least 5 examinations under basic exchange and full emotional and physical comfort. Next, examination of the heart's current state is made and the diagnostic criteria (DC) are calculated as the averaged amount of points of the mentioned parameters according to 4 points scale: normal range (0), minor (1), moderate (2), severe (3) damage. The current heart state is compared with individual norm for a particular person, and if individual norm is absent the comparison is made of universal sex-and-age norm. In result, it is concluded that human heart is in normal state (minor, moderate or severe damage), if current DC as compared to the reference state is within the range of $0 \leq DC < 0.5$ ($0.5 \leq DC < 1.5$, $1.5 \leq DC < 2.5$ or $2.5 \leq DC < 3$). Furthermore, if any damages in the heart functional state are revealed, the recommendations are provided respectively: when minor damages—to change life style and/or intensity/nature of work, when moderate damage—the same doings and to consult a doctor as regularly you do, when severe damage—to seek urgently for doctor consultancy.

The advantages of UA 61 285 is the combination of different parameters obtained through the analysis of the averaged ECG curve and HRV parameters; to make synthesis of the general DC, to apply 4-value decision rule that allow reveal 3 degrees of heart damages from normal range. The disadvantage of the said method is the use of relatively simple parameters but not advanced parameters, i.e. 4th generation ECG.

This deficiency is taken into account in WO 2014/098784 A1 [A61B 5/0404, I. Chaykovskyy, M. Budnyk, B. Vasyliev et al, Fourth generation portable intellectual electrocardiograph, 2014]. According to this invention the ECG signals are registered at least in the one from 12 standard ECG leads, the device include set of standard ECG electrodes, ECG cable, electronic block of registration & signal processing, USB cable, portable computer and software. ECG signals are transmitted from the unit to the computer via USB cable, and then are displayed on the screen, automatically processed and analyzed, and the software carries out medical analysis of ECG signals.

This device differs from those that the unit is composed of high integration degree chip and high-end functionality, also microcontroller chip is employed to be served as embedded microprocessor control unit; no control means are installed on the top cover of the unit; power supply and control signals are transferred to the computer via USB cable; the software include medical analysis algorithms and ECG of the 4th generation; recording and signal processing is performed in SCP-ECG digital format intended for data transmitting into computer networks and for telemedicine.

WO 2014/098784 advantage lies in implementation of CVS diagnosis based on ECG 4th generation, and its disadvantage is that in the present invention the 4th generation diagnostic methods are not disclosed.

Invention UA 108766 [A61B 5/02, A61B 5/0402, Method for assessment of human CVS functional state, I. A. Chaikovsky, V. A. Denysiuk, 2015] is taken as prototype under which ECG is recorded, quantitative ECG, HRV, HR disorders parameters are calculated; averaged ECG is assessed by various mathematical methods; several DC are calculated; 4-digit scale (normal range, minor, moderate and severe damages) is applied.

In method normalized parameters are calculated by scaling quantitative ECG parameters to 0-100 points range, 4 levels hierarchical structure is set where level 1 stands for plural number of the said normalized parameters. Level 2 forms 6 groups of relative indicators having close physiological nature including amplitude-time ECG parameters (group 1) for current control of myocardium state, HRV indicators (group 2) for current control of CVS regulation, indicators of HR abnormalities (group 3) for current control of CVS, amplitude-time ECG parameters (group 4) to evaluate myocardium reserves, HRV parameters (group 5) for current control of reserves of CVS regulation, indicators for HR abnormalities (group 6) to evaluate CVS reserves, 6 general indicators are calculated by averaging parameters of each group.

The 3rd level cover calculations of 3 integral DC for assessment: DC1—myocardium state as an average of indices (1) & (4), DC2—CVS regulation as an average of indices (2) & (5), DC3—diagnostics HR abnormalities as an average of indicators (3) & (6). The 4th level covers calculation of integral DC by averaging DC1 . . . 3 and making decision that CVS is in normal state (minor, moderate or severe damage), if the integral DC are within the range of $75 \leq DC \leq 100$ ($50 \leq DC < 75$ $25 \leq DC < 50$ or $DC < 25$), all actions are computer-aided, results are displayed and printed out.

The advantage prototype is structuring ECG and HRV parameters by 4 levels according to degree of generalization. Disadvantages of it is lack of:
 1) advanced 4th generation diagnostic indicators,
 2) aggregation of known routine and the advanced indicators, and original indicators proposed by the authors,
 3) forecast for the CVS state,
 4) evaluation of human emotional state,
 5) produce of aggregated decision with taking into account both known diagnostic codes and ECG parameters of 4th generation.

Thus, a deficiency of modern technology is the lack of universal comprehensive evaluation method for functional state of human CVS based on combination of known diagnostic codes, ECG 4th generation and integral index. This limits the stratification of the CVS states in detailed manner and accuracy in diagnostics of damages.

SUMMARY OF THE INVENTION

The essence of proposed technical solution lies in methodologies employed to calculate the quantitative ECG indicators, putting them in right order and to produce aggregated diagnosis on the basis of 4-value decision rule.

Invention is based on the task of improving ECG universal scoring evaluation method via recording ECG; calculating both quantitative ECG parameters by various mathematical methods and HRV parameters; calculating deviations from the normal range under 4-value rule: normal range, minor, moderate, severe damages, and thereupon to asses abnormalities of the CVS and human emotional state.

Assigned task is achieved by:
 1) human ECG registration at least within 6 leads,
 2) creating of hierarchical diagnostic algorithm covering 5 levels where each next level is established by averaging the indicators or aggregated decisions obtained at the previous level,
 3) Level 1—calculation of the normalized ECG parameters by scaling quantitative ECG parameters according to the range from 0 to 100 points,
 4) Level 2—dividing above normalized indicators into at least 7 groups of relative indicators of close physiological nature including:
 a) group 1 of amplitude-time ECG indicators intended to current control of myocardium state, b) group 2 of HRV indicators to current control of CVS regulation, c) group 3 of indicators of cardiac arrhythmias to current control of CVS, group 4 of amplitude-time ECG indicators for estimation of myocardial reserves, group 5 of HRV indicators to control reserves of CVS regulation, f) group 6 of HRV indicators to control psycho-emotional state, g) group 7 of indicators of HR abnormalities to assess CVS reserves, 5) calculation of at least 7 general indicators 1, 2, 3 . . . 7 via averaging values of indicators of respective group 1, 2, 3 . . . 7, 6) at Level 3 to calculate 4 integral DC1-DC4 that include:

a) DC1 forevaluation of myocardium state as the average out of general indicators 1 and, b) DC2 for evaluation of CVS regulation as the average out of general indicators 2 and 5, c) DC3 for evaluation of HR disorders as the average out of general indicators 3 and 7, d) DC4 for evaluation of emotional state as a general indicator 6, 7) calculation of the complex index of functional state (CIFS) of the CVS as the average value out of 4 integral indicators DC1-DC4, 8) calculating the known ECG scores based on syndrome-based analysis by Hannover algorithm and Minnesota code, 9) calculating the known ECG scores based on the following:

a) myocardial abnormalities codes, such as Silvester code, Q-code, CIIS code, and Aldridge code, b) prediction codes of serious cardiovascular events such as Froelicher code, 1st lead code, AVR lead code, and code of sudden cardiac death, 10) at Level 4 making an intermediate diagnostic decision that CVS functional state is in normal range (minor, moderate or severe damages) if CIFS values are in range of $76 \leq CIFS \leq 100$ ($51 \leq CIFS \leq 75$, $26 \leq CIFS \leq 50$ or $0 \leq CIFS \leq 25$), 11) making intermediate diagnostic or prognostic decisions according to above 4-value rule, including:

a) diagnostic decision based on Hannover algorithm, b) diagnostic decision based on Minnesota code, c) diagnostic decision based on myocardial abnormalities codes, d) prognostic decision based on prediction codes of serious cardiovascular events, 12) at Level 5: final aggregated diagnostic and prognostic decision about CVS functional state and psycho-emotional state is made via combination of intermediate decision based on CIFS with at least one intermediate decision based on Hannover algorithm, Minnesota code, myocardial abnormalities codes, or prediction codes of serious cardiovascular events, 13) all above steps is made in computer-based manner with subsequent visualization onto PC monitor and hard-copy printing of evaluation results.

14) at the Level 1 ECG indicators of the 4th generation are calculated.

15) at the Level 3 the syndrome-based ECG analysis is made with help of the another well-known algorithm instead of the Hannover algorithm.

The novelty of proposed invention are:

1. Use of new diagnostic ECG parameters of 4th generation.

2. Aggregation of the known ECG routine indicators, 4th generation ones, and original general indicators proposed by the authors at Level 3.

3. Application of separate group of prognostic indicators.

4. Input into consideration 7-th group of indicators and general DC to assess human psycho-emotional state in quantitative manner.

5. 5th Level is added to produce aggregated decision by taking into account as complex index CIFS so as the known diagnostic codes.

The technical result are following:

1. Simultaneous diagnostics of abnormalities in CVS and emotional state.

2. Give possibility to make both diagnostic and prognostic decision.

3. Increasing accuracy and reliability of diagnostics.

4. Diagnosis is more detailed due to identification of most vulnerable areas of CVS, such as state of regulation of vegetative balance.

Every distinctive feature of the proposed method is deemed essential and the all together are sufficient enough to achieve the task. The cause-and-effect link exists between the distinctive features of the proposed invention and the obtained technical result.

The combination of distinctive features is non-obvious to a specialist dealing within this technical field and is significant step towards diagnosis of CVS pathologies while taking into account the human emotional state and its influence on CVS operation.

BRIEF DESCRIPTION OF THE DRAWINGS

FIG. 2. Groups of indicators with close physiological nature for three examined subjects (2nd Level).

FIG. 3. General indicators, diagnostic criteria and their quality grading for three examined subjects (2nd and 3rd Levels).

FIG. 4. Diagnostic criteria, known diagnostic codes, intermediate and final decisions for the three examined subjects (4th and 5th Levels).

DESCRIPTION OF THE PREFERRED EMBODIMENTS

Figure 1:
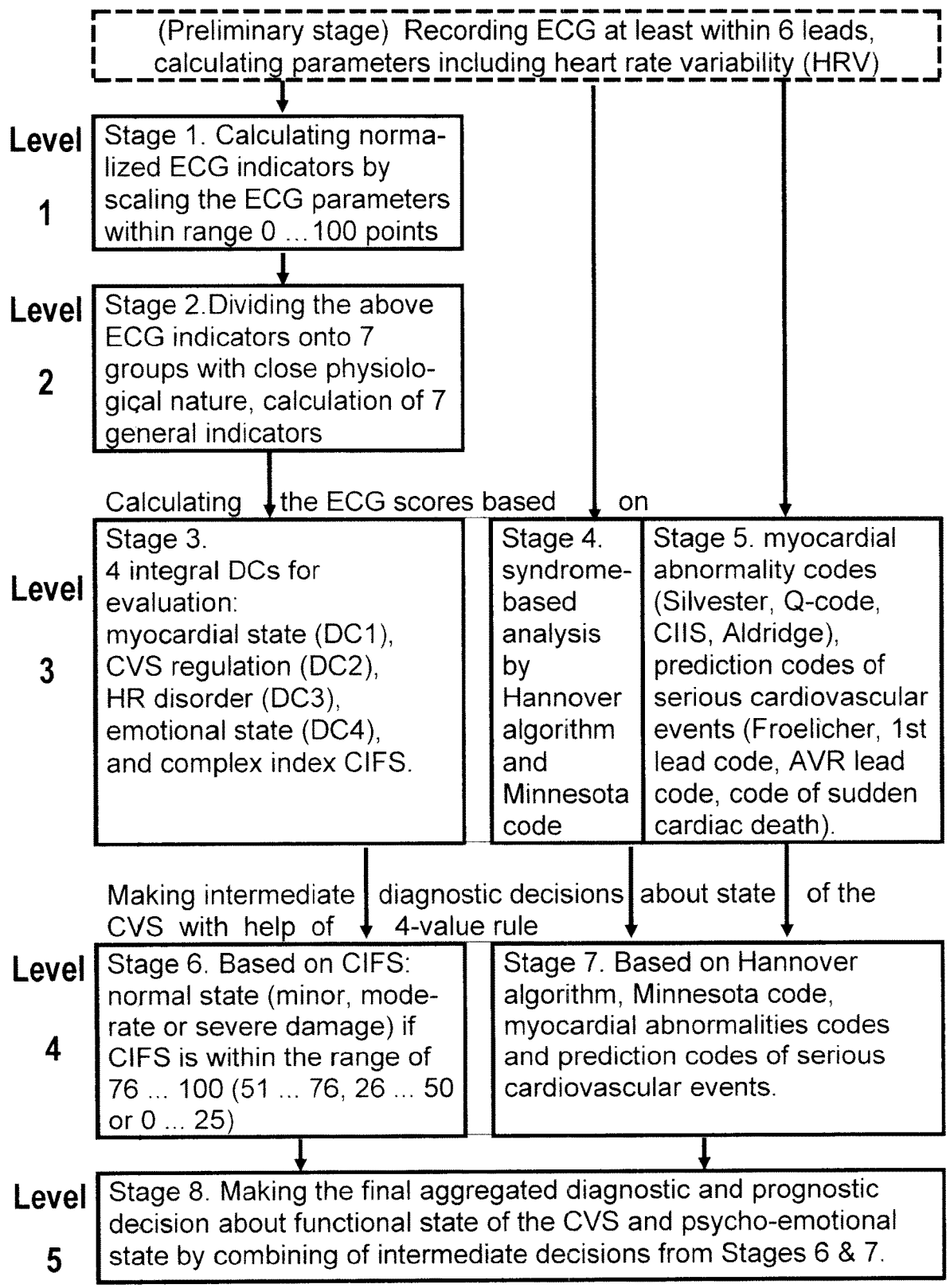
FIG. 1. Flow-chart of proposed diagnostic algorithm.

Basic embodiment of method contains action sequence, executing individual steps of the algorithm, which in consumption implement proposed method. Schematic diagram of the method is represented on FIG. 1, where dashed stage don't describe proposed method, but represented just to illustrate its background.

Preliminary Stage (Registration and Calculation of ECG Parameters)

1) Patient ECG registration during a period not less than 2 minutes within 6 standard leads.

2) Calculation of average cardiocycle, HRV parameters and signs of disorders in frequency, rhythm and sequence of heart beats, 3) Evaluation of average ECG on the basis of amplitude-time parameters and integrals (areas) of all elements of ECG curve.

4) Calculating parameters by using various mathematical methods.

Steps 1-4 are known and similar to those disclosed in prototype UA 108766, and are given only to illustrate the embodiment. The proposed method is a hierarchical algorithm comprising of 5 quality levels.

Calculation stage (1st, 2nd and 3rd Level)

Level 1—obtaining a set of 148 normalized ECG indicators.

Stage 1. Normalization of ECG parameters according to scale ranging from 0 to 100 points.

Level 2—obtaining a set of general indicators.

Stage 2. Dividing normalized indicators onto 7 relative groups of with close physiological nature, calculation of 7 general respective indicators.

Level 3—obtaining DC and complex index of functional state (CIFS)

Stage 3. Calculation of 4 diagnostic criteria (DCs) and CIFS:
 a) DC 1—to evaluate CVS regulation,
 b) DC2—to evaluate myocardial state,
 c) DC3—to evaluate HR disorder,
 d) DC4—to evaluate emotional state
 e) CIFS as arithmetic average of DC1 . . . 4.

Stage 4. Calculation of ECG score based on syndrome-based analysis to be carried out by using the Hannover algorithm and Minnesota code.

Stage 5. Calculation of ECG score based on myocardial abnormalities codes (Silvester code, Q-code code, CIIS code, Aldridge code) and prediction codes of serious cardiovascular events (Froelicher code, 1st lead code, AVR lead code, predict code of sudden cardiac death).

Medical opinion stage (4th and 5th Levels)

4th Level—making intermediate decisions

Stage 6. Making intermediate decision based on CIFS (similar as to the prototype). CIFS values for current state are compared with individual reference value for a particular subject, if absent—with universal sex-and-age reference value. Making decision that the CVS functional state is in normal range (minor, moderately or severe damage) if CIFS value is within the range of 76≤FSAF≤100 (51≤FSAF≤75, 26≤FSAF≤50 or 0≤FSAF≤25).

Stage 7. Making intermediate decision based on Hannover algorithm, Minnesota code, myocardial abnormalities codes and prediction codes of serious cardiovascular events.

Level 5—Making final decision.

Stage 8. Aggregated diagnostics & prognostic decision about functional state of CVS and psycho-emotional state is made by combining intermediate decisions based on CIFS, Hannover algorithm, Minnesota code, myocardial abnormalities codes, prediction codes of serious cardiovascular events.

The proposed algorithm is shown in FIG. 1 and covers 8 stages. Level 1—"norm-based indicators" (Stage 1). Level 2—"generalized indicators" (Stage 2). Level 3 "general indicators" includes 3 stages: 4 Integrated DC and CIFS (Stage 3), ECG scoring based on Hannover algorithm, Minnesota code (Stage 4), ECG scoring based on myocardial abnormalities codes and prediction codes of serious cardiovascular events (Stage 5).

Level 4 "intermediate decisions" includes 2 stages: making intermediate decision based on CIFS (Step 6) and Hannover algorithm, Minnesota code, myocardial abnormalities codes and prediction codes of serious cardiovascular events (Stage 7). Level 5 "final decisions" is performed based on combination of 5 intermediate decisions obtained at Level 4 (Stage 8).

For the demonstration purpose the FIG. 2 gives 14 indicators of Level 1 for three subjects. They cover heart rate, SDNN, RMSSD, stress index, triangular index, emotional state the index, PNN50, vegetative balance, vasomotor activity cycle regulation, basal activity levels regulation, entropy and fractal index, functional classes according to Baevsky and according to Mashyn. These parameters describe the following:
 a) different aspects of heart rate variability,
 b) amplitude-time parameters and shape of ECG peaks,
 c) presence of main disorders in frequency, rhythm and sequence of myocardium contractions (in otherwords—heart rhythm disturbances).

Also 12 indicators are calculated that describe the myocardium state on the basis of ECG form within 6 leads: 4 integral indicator of ST-T form for I, III, AvL, AvR leads, 6 indexes describing amplitude and area for I, II, III, AvL, AvR, AvF leads and shape of ECG peaks, ECG intervals duration index, QRS-T angle in the frontal plane.

FIG. 3 gives the $2^{nd}$ Level including 2 groups of relative indicators having close physiological nature. For example, indicators of "current control regulation", "regulation reserves state" and "integral indicators" are mainly reflect current, i.e. instantaneous cardiovascular functional state. This group characterizes real-time adaptive response to external stimulations.

Another group (4 indicators) is current control of myocardial state, myocardial reserve state, stationarity index for myocardium, in-depth ECG analysis (6 leads). It mainly reflects the level of functional reserve to be spent for adaptation.

Level 3 (FIG. 4) covers 7 general indicators and 4 integral DC reflecting various aspects of the CVS functioning. These indicators are: 1) regulation, 2) myocardium states (6 leads), 3) HR abnormalities obtained as result of evaluation of myocardial regulation by nervous system, myocardial, state and HR abnormalities diagnostics, and 4) DC for assessment of human emotional state.

Then, universal indicator of CVS functional state is calculated in a form of complex index CIFS (FIG. 4). This Figure also shows the values of other codes and related intermediate diagnoses that are obtained at Level 4 of the analysis, and also the final aggregated diagnose.

There are 3 examples are presented to illustrate the method as to the examined subjects with different CVS disorders.

Medical Case 1. Thus, upon the results of hierarchical evaluation of heart of Patient B has been found the following: Indicators of Level 1: SDNN is slightly decreased, stress index is slightly increased, other indicators are normal range. Almost all general indicators of Level 2 are also in normal range within 80-96 points, except for "myocardium reserve state assessment" indicator (65 points) giving a minor damage.

As a result, all DCs at Level 3 are located in normal range: DC1 "myocardium state"—80 points, DC2 "CVS regulation"—94 points, DC3 "HR disorder"—85 points, i.e. no such disorders have been found, and DC4 "emotional state assessment"—80 points.

As the result, CIFS for Patient B is of 85 points evidencing that CVS is in normal range. Hannover algorithm and Minnesota code also give 100 points, intermediate diagnose based on other codes (for myocardial abnormalities and for serious cardiovascular events) also indicate "normal range". Total points scale evaluation of Patient B functional state and the emotional state is equal to 91 points which gives aggregate diagnose—"normal state".

Medical Case 2. As to the examined subject 0301 it is necessary to pay attention to such indicator of Level 1 as the ECG ratio index and to the general indicator of Level 2 "current control of myocardium", according to which "moderate damages" took place. DC1 of Level 3 "myocardium state" is 70 points, i.e. "minor damages" but other indicators of Level 3 are in normal range as well as CIFS is equal to 79 points.

Assessment under Hannover algorithm gives 75 points and mostly other codes give intermediate diagnose—"minor damage", only Minnesota code is equal to 50 indicating about "minor damages". Overall points assessment is equal to 72 points which gives the final decision as "minor damages".

Medical Case 3. In contrast, the examined subject 0304 has 47 points of CIFS indicator and according to Hannover algorithm he/she has 50 points, and, like for most of other codes, gives decision "moderate damages". Only a few codes including the Minnesota code indicate the minor damages, but their points only slightly higher than 50. The total score is equal to 49, which gives aggregate decision as "moderate damages".

Within additional embodiment at Level 1 an additional calculation of ECG parameters of 4th generation has been done, for example, QRS high-frequency analysis, T-wave analysis based on SVD, late potentials analysis, QRS-T angle analysis or another parameter.

In another embodiment at Level 3 the ECG syndrome-based analysis has been performed based on another well-known algorithm, for instance, Washington algorithm or another one instead of Hannover algorithm.

In all embodiments the registration and signal analysis is performed with help of computer program "Cardio Multimoda 1" and the obtained results are to be displayed and printed out respectively.

The advantage of this method is that at the transition to higher level the information, which obtained at the previous level, is generalized and aggregated. These actions are expressed in averaging the points of the previous level indicators. It means that indicators obtained at Level 1 are averaged at Level 2, and the indicators of Level 2 are averaged at Level 3. In so doing the specific aspects of screening study are taken into account whose main purpose is to identify latent pathological changes, search for indications to conduct further and more in-depth study.

In all preferred embodiments diagnostic results are summarised in table including HRV, myocardium state, and HR disorders indicators and also decision as well as blocks of integral assessment of regulation, myocardium state, HR disorders and CIFS block are displayed in graphic form.

Data analysis of FIG. 2-4 shows that different indicators "feel" in different way the damages of various types and major part of them cover almost all damage types. This suggests consider this method as universal.

All indicators are presented in a quantitative way and colour coding for functional state grading is applied. In so doing the normal range of indicators are coloured in green, minor damages—in yellow, moderate ones—in orange, and severe damages—in red.

The advanced approaches being applied to diagnose under hierarchical principle and to present the indicators of human CVS in quantitative and colour representation make possible to improve informative value and clarity of the diagnostic results for a wider range of users.

The proposed invention is industrially applicable because it requires digital electrocardiograph, portable computers such as notebook, printer and software. No specific requirements are set to the computer and printer; any products available at the market are welcomed.

The basic embodiment applies portable intellectual electrocardiograph «CARDIOLYSE» ("Cardiolyse" LLC, Kyiv, Ukraine). It is possible to apply other equipment being available at the market to input the data via USB interface. Numerical algorithms are implemented in software registered at Ukrainian Agency on Copyright & Related Rights [Program for registration and analysis of small-channel ECG signals "Multymoda Cardio 1", I. Chaykovskyy, V. Vasyliev, Yu. Frolov, M. Dordiienko, Copyright Certificate for computer program #47857 from 18 Feb. 2013].

The particular embodiments of the method in the invention are presented in detail for illustrative purposes only. It is clear, that in practice, specialists and other users who are experienced in cardiology, ECG analysis and CVS state can introduce some changes and modifications into, for example, to apply different procedure to structure the indicators, to apply another approach to normalise and calculate DC according to hierarchy level. However, we consider that both the said changes and modifications, and others ones, to be done without significant differences from the essence and claims of proposed invention, fall under this patent.

The invention claimed is:
1. Method of electrocardiogram (ECG) evaluation based on a universal scoring system, comprising recording electrocardiogram (ECG) signals from at least 6 leads,
    calculating qualitative parameters of the ECG signals, including heart rate variability (HRV),
    calculating diagnostic criteria (DC) and their deviations from a norm by using a 4-value rule: normal range, minor, moderate, severe damages, and
    evaluating abnormalities in cardiovascular system (CVS) and emotional state of person
characterized in that a hierarchical 5-level diagnostic algorithm is made, in which each next level is formed by averaging indicators or combining decisions obtained at a previous level,
Level 1—calculation of normalized ECG indicators via scaling of quantitative ECG parameters according to a range from 0 to 100 points,
Level 2—dividing above ECG indicators into at least 7 groups of relative indicators with close physiological nature, including:
    Group 1 of amplitude-time ECG indicators to current control of myocardium state,
    Group 2 of HRV indicators to current control over CVS regulation,
    Group 3 of heart rate (HR) disorder indicators to control of the CVS state,
    Group 4 of amplitude-time ECG indicators for evaluation of myocardial reserves,
    Group 5 of HRV indicators for evaluation of reserves of the CVS regulation,
    Group 6 of HRV indicators to evaluate human psycho-emotional state,
    Group 7 of HR disorder indicators for evaluation of CVS reserves,
calculating at least 7 general indicators 1, 2, 3 . . . 7 by averaging values of the respective Groups 1, 2, 3 . . . 7,
Level 3—calculating 4 integral DCs, which include:
    DC 1 for evaluation of myocardium state as an average of general indicators 1 and 4,
    DC2 for evaluation of CVS regulation an average of general indicators 2 and 5,
    DC3 for evaluation of HR disorders as an average of general indicators 3 and 7,
    DC4 for evaluation of emotional state as a general indicator 6,
calculation of a complex index of functional state (CIFS) of the CVS as an average value of 4 integral indicators

DC1-DC4, calculating a known ECG score based on syndrome-based analysis by Hannover algorithm and Minnesota code, calculating known ECG scores based on the following:
- myocardial abnormalities codes, namely, Silvester code, Q-code, CIIS code, and Aldridge code,
- prediction codes of serious cardiovascular events such as Froelicher code, 1st lead code, AVR lead code, and code of sudden cardiac death, Level 4—making an intermediate diagnostic decision that CVS functional state is in normal range (minor, moderate or severe damages) when CIFS values are in range of 76 CIFS 100 (51 CIFS 75, 26 CIFS 50 or 0 CIFS 25),
- making intermediate diagnostic decision according to mentioned 4-value rule based on Hannover algorithm, Minnesota code, and myocardial abnormalities codes,
- making intermediate prognostic decisions according to mentioned 4-value rule based on prediction codes of said serious cardiovascular events, Level 5—making a final aggregated diagnostic and prognostic decision about CVS functional state and psycho-emotional state by combination of intermediate decision based on CIFS with at least one intermediate decision based on Hannover algorithm, Minnesota code, myocardial abnormalities codes, or prediction codes of serious cardiovascular events, performing all above steps using a computer processor and printing a hard-copy of evaluation results.

2. Method of ECG evaluation according to claim 1 characterized in that at the Level 1 ECG indicators of a 4th generation are calculated, namely, QRS high-frequency analysis, T-wave analysis based on single value decomposition (SVD), late potential analysis, and QRS-T angle analysis.

3. Method according to claim 1 or 2 characterized in that at the Level 3 the syndrome-based ECG analysis is made with help of Washington algorithm instead of the Hannover algorithm.

* * * * *